United States Patent
Garamszegi et al.

(10) Patent No.: US 12,426,925 B2
(45) Date of Patent: *Sep. 30, 2025

(54) HYBRID RADIOLUCENT SURGICAL OPERATING TUBE

(71) Applicant: Aurora Spine, Inc., Carlsbad, CA (US)

(72) Inventors: Laszlo Garamszegi, Mission Viejo, CA (US); Trent James Northcutt, Oceanside, CA (US); Jeremi Leasure, Carlsbad, CA (US)

(73) Assignee: Aurora Spine, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/388,251

(22) Filed: Nov. 9, 2023

(65) Prior Publication Data
US 2024/0081874 A1    Mar. 14, 2024

Related U.S. Application Data

(63) Continuation of application No. 17/676,633, filed on Feb. 21, 2022, now Pat. No. 11,832,853.

(60) Provisional application No. 63/152,127, filed on Feb. 22, 2021.

(51) Int. Cl.
*A61B 17/70* (2006.01)
*A61B 90/00* (2016.01)
*A61F 2/30* (2006.01)

(52) U.S. Cl.
CPC ......... *A61B 17/7055* (2013.01); *A61B 90/39* (2016.02); *A61B 2090/3966* (2016.02); *A61F 2002/30622* (2013.01); *A61F 2002/30995* (2013.01)

(58) Field of Classification Search
CPC . A61B 17/7055; A61B 17/88; A61B 17/3421; A61B 2017/3454; A61B 90/39; A61B 2090/3966; A61F 2002/30995; A61M 29/00
USPC ...................................... 606/96, 97
See application file for complete search history.

(56) References Cited

U.S. PATENT DOCUMENTS 11,832,853 B2 * 12/2023 Garamszegi .......... A61F 2/4603
2013/0267989 A1 * 10/2013 Mauldin ............... A61M 29/00
                                                       606/86 R

* cited by examiner

*Primary Examiner* — Eduardo C Robert
*Assistant Examiner* — Christina Negrellirodriguez
(74) *Attorney, Agent, or Firm* — Hybrid Law Group P.C.

(57) ABSTRACT

An apparatus for sacroiliac fusion surgery is provided. The apparatus includes a tube that allows x-ray visualization of objects passing through the tube, the tube having a proximal end with an opening and a distal end with an opening. The tube further has one or more mounts on its distal end for attaching removable anchoring tips thereto. The apparatus further has one or more removable anchoring tips attached to the distal end of the tube with the one or more mounts. The tube is made of a material that is radiolucent and permits x-ray visualization of objects that are passed through the tube.

8 Claims, 4 Drawing Sheets

HYBRID RADIOLUCENT SURGICAL OPERATING TUBE

RELATED APPLICATIONS

This application is a continuation of U.S. Ser. No. 17/676,633, filed Feb. 21, 2022 which claims priority from U.S. Provisional Patent Application Ser. No. 63/152,127, filed Feb. 22, 2021, both are incorporated herein by reference in their entirety.

BACKGROUND

This invention relates generally to the field of orthopedic surgery involving imaging during the surgical procedure for the proper placement of surgical tools, guides, and implants.

Metal operating tubes have been used in orthopedic surgery procedures for a long time. They have been used in laparoscopic and mainly minimally invasive surgical procedures. Surgical tubes are typically made of metal for durability. The disadvantage of metal surgical tubes is that they are not transparent in x-ray imaging or other imagining. Thus, any instruments passed through them cannot be seen in an x-ray image during the procedure while they are inside the tube. Metal tubes block the view of depth dependent surgical instruments that are passed through the tubes. Thus, surgeons are unable to see what the status of the tool is unless they use other references to determine tool position.

One example of a surgical procedure that suffers from visualization impediments is sacroiliac fusion surgery. This type of orthopedic surgery requires x-ray visualization during the procedure in order to locate the sacroiliac joint and the proper placement of guides, instruments, and implants to the appropriate position within the joint for optimum fusion and pain relief. Tubes that are used now are metal, and guides, instruments and implants that are passed through these tubes cannot be visualized while they are in the tubes.

There is a need for orthopedic surgical operating tubes that allow for visualization of instruments that pass through the tubes and a need for improvement surgical methods that allow better x-ray and other types of visualization of surgical guides, instruments and implants during the surgical procedure.

SUMMARY

One object of the invention is to provide a radiolucent surgical apparatus for sacroiliac fusion surgery that allows clear x-ray imaging without shielding visibility of surgical tools used in implanting permanent implants.

Another object of the invention is to allow surgeons to utilize direct vision seeing surgical instruments instead of using multiple reference methods to assume the locations and depths of surgical instruments.

Another object of the invention is to allow a better surgical operating tube that allows for less need to rely on harmful radiation during imaging.

In one embodiment, a radiolucent surgical apparatus for sacroiliac fusion surgery is provided, which allows clear x-ray imaging without shielding visibility or surgical tools used in implanting permanent implants. The apparatus includes a tube that allows x-ray visualization of objects passing through the tube, the tube having a proximal end with an opening and a distal end with an opening. The tube further has one or more mounts on its distal end for attaching removable anchoring tips thereto. The apparatus further has one or more removable anchoring tips attached to the distal end of the tube with the one or more mounts. The tube is made of a material that is radiolucent and permits x-ray visualization of objects that are passed through the tube.

In another embodiment, a method of performing an orthopedic surgical procedure is provided. The method includes locating a site of intervention using x-ray or other form of radiographic imaging; inserting a guide pin through an incision and advancing a distal end of the guide pin to the site of intervention; guiding an open distal end of a radiolucent tube over the guide pin and advancing the tube to the site of intervention, wherein the guide pin is visible in a radiographic image of the tube and guide pin even though the guide pin is inside a lumen of the tube; securing the distal end of the radiolucent tube to the site of intervention; and inserting one or more objects through an open proximal end of the radiolucent tube and advancing said one or more objects through the lumen of the tube to the site of intervention, wherein said one or more objects are visible in a radiographic image of the tube even when said one or more objects are inside the lumen of the tube.

In yet another embodiment, a method of performing a sacroiliac fusion procedure is provided. The method includes locating the sacroiliac joint using radiographic imaging; inserting a guide pin through an incision on the subject and advancing the guide pin to the sacroiliac joint; and providing a tube that allows x-ray visualization of objects passing through the tube. The tube has a proximal end with an opening; a distal end with an opening; one or more mounts on the distal end of the tube for attaching removable anchoring tips thereto; and one or more removable anchoring tips attached to the distal end of the tube with the one or more mounts. The tube is made of a material that is radiolucent and permits x-ray visualization of objects that are passed through the tube. The method further includes guiding the distal opening of the radiolucent tube over the guide pin and advancing the tube to the site of sacroiliac joint, wherein the guide pin is visible in the radiographic image of the tube and guide pin even though the guide pin is inside a lumen of the tube; securing the distal end of the radiolucent tube to the sacroiliac joint by forcing the anchoring tips into the sacroiliac joint; and inserting one or more objects through the proximal opening off the radiolucent tube and advancing said one or more objects through the lumen of the tube to the sacroiliac joint, wherein said one or more objects are visible in a radiographic image of the tube even when said one or more objects are inside the lumen of the tube.

Other objects and advantages of the present invention will become apparent from the following descriptions, taken in connection with the accompanying drawings, wherein, by way of illustration and example, various embodiments of the present invention are disclosed.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION

Exemplary embodiments of the invention are shown in the accompanying figures and described below.

Figure 1:
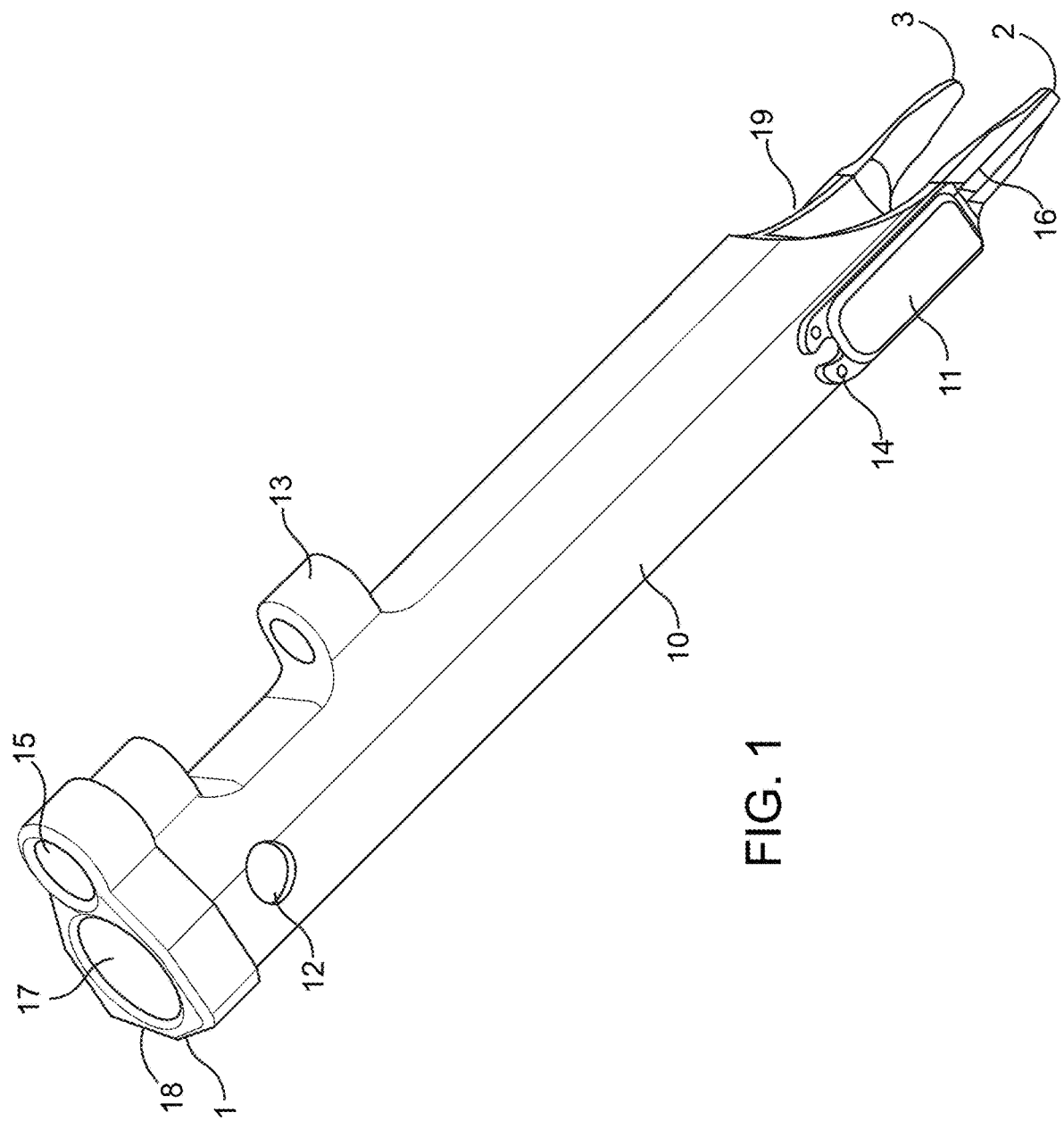
FIG. 1 is a perspective view of a radiolucent tube used for orthopedic surgical procedures, such as a sacroiliac fusion procedure.

FIG. 1 provides a perspective view of one embodiment of a radiolucent surgical operating tube 1. Tube 1 is made of a radiolucent material, which means that the material is partly or wholly permeable to radiation, particularly x-rays. Radiolucent material is transparent to x-rays, because it is less dense than radiopaque materials and permits x-ray beams to pass through the material. Radiopaque materials appear light or white in radiographic images, whereas radiolucent materials are transparent in radiographic images. For example, an object passing through the lumen of a radiopaque tube would not be visible in a radiographic image until it exits the tube. However, an object passing through the lumen of a radiolucent tube is visible in a radiographic image even while it is inside the lumen of the tube.

Tube 1 is a radiolucent surgical operating tool for minimally invasive sacroiliac fusion surgery and includes a hollow body 10 made of any material that is radiolucent on x-ray (or other radiographic) images and does not block the visibility of surgical instruments or other objects that enter the lumen 17 of tube 1 to do tissue and bone preparation and dissection work followed by implantation of a final implant, such as bone graft material or pins.

Tube 1 has a proximal end with opening 18 that leads into lumen 17 of tube 1, and a distal end with opening 19 that leads out of lumen 17 of tube 1. Various objects can be passed through lumen 17 of tube 1, and because tube 1 is made of a radiolucent material, those objects are visible and can be visualized with x-ray imaging. Thus, they are visible in radiographic images of tube 1. At the distal end of tube 1 are removable anchoring tips (or blades) 2 and 3. Removable anchoring tips 2 and 3 have an outer side or surface and an inner side or surface. The outer side or surface of anchoring tips 2 and 3 have channels 16 formed therein. Channels 16 are configured to secure anchoring tips 2 and 3 to the sacroiliac joint by cutting into the bone or cartilage at the joint when distal end 19 of tube 1 is forced into the joint. Tube 1 has a main hollow body 10, which is radiolucent. Tube 1 has mountings 11, one mounting 11 on each side of main hollow body 10. Removable anchoring tips 2 and 3 are mounted to main body 10 by being clipped onto mountings 11 with clips 14. Clips 14 and mountings 11 form a quick-change retaining mechanism. Two opposing arms of each of clips 14 can bend slightly away from each other when forced apart from each other using a tool. By forcing the two opposing arms of clips 14 away from each other, anchoring tips 2 and 3 can be detached from mountings 11. Anchoring tips 2 and 3 can be attached to mountings 11 by sliding the opposing arms of clips 14 over mountings 11, which securely attaches anchoring tips 2 and 3 to mountings 11 unless a force is applied to spread the two opposing arms of clips 14 away from each other while applying a pushing force in the distal direction to push clips 14 off of mountings 11. This forms a quick change retaining/removing mechanism for anchoring tips 2 and 3. Main body 10 has attachment slots 12 (one on each side of hollow main body 10) to which surgical tools or rods can be attached in order to insert or remove tube 1 from a surgical site. Slots 12 also serve as visual references that allow laser marked reference points to be visible of other surgical tools entering lumen 17 of tube 1. Tube 1 also has separate openings 15 and 13 that receive a guide pin or anchoring pin. The guide pin or anchoring pin can be used to secure tube 1 to bone. While tube 10 is radiolucent, anchoring tips 2 and 3 may also be radiolucent. Alternatively, anchoring tips 2 and 3 can be made of a material that is radiopaque, such as various medical/surgical grade metals, which allows them to be visible in x-ray or other radiographic images.

Figure 2A:
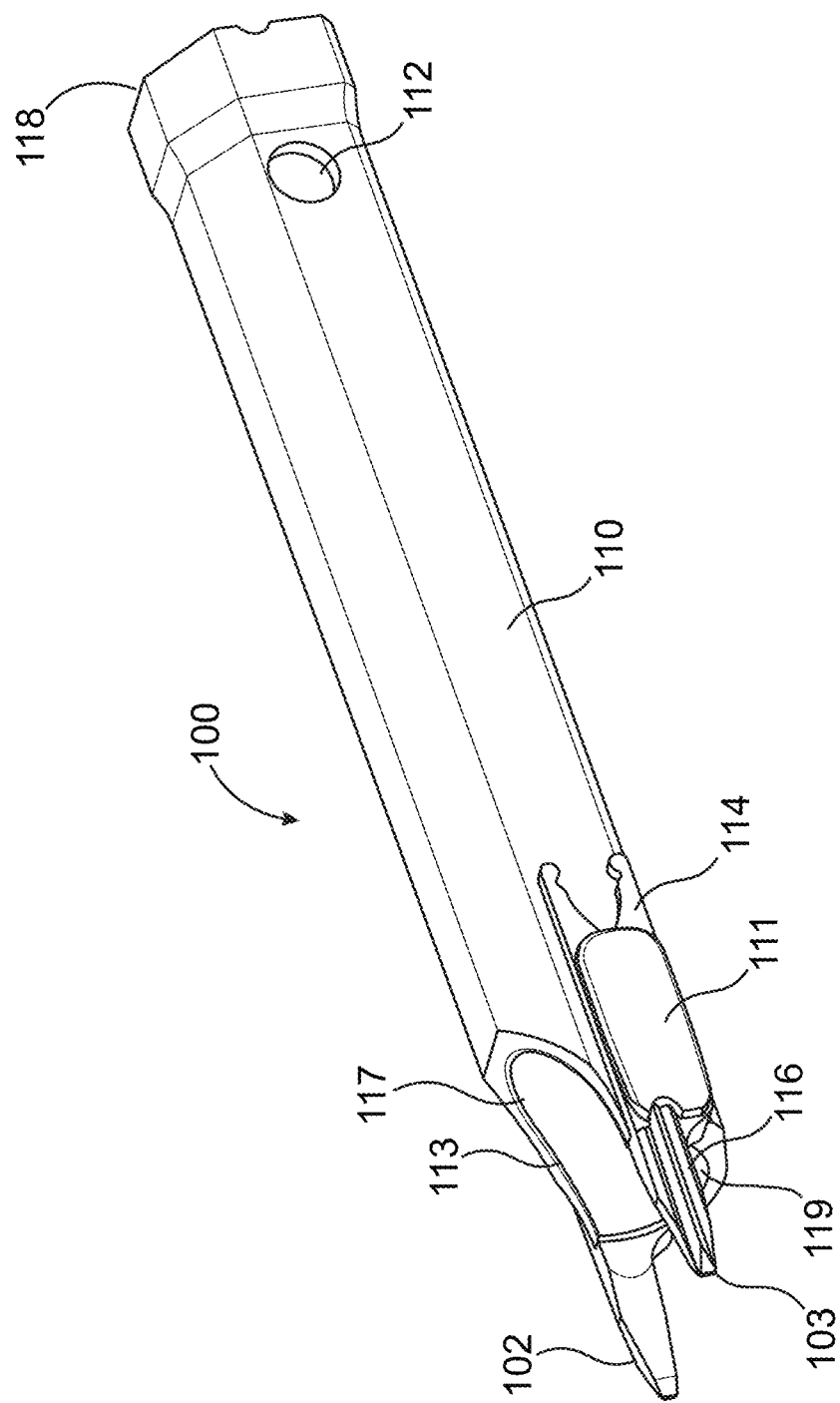
FIG. 2A is a perspective view of another embodiment of a radiolucent tube used for orthopedic surgical procedures, such as a sacroiliac fusion procedure.
Figure 2B:
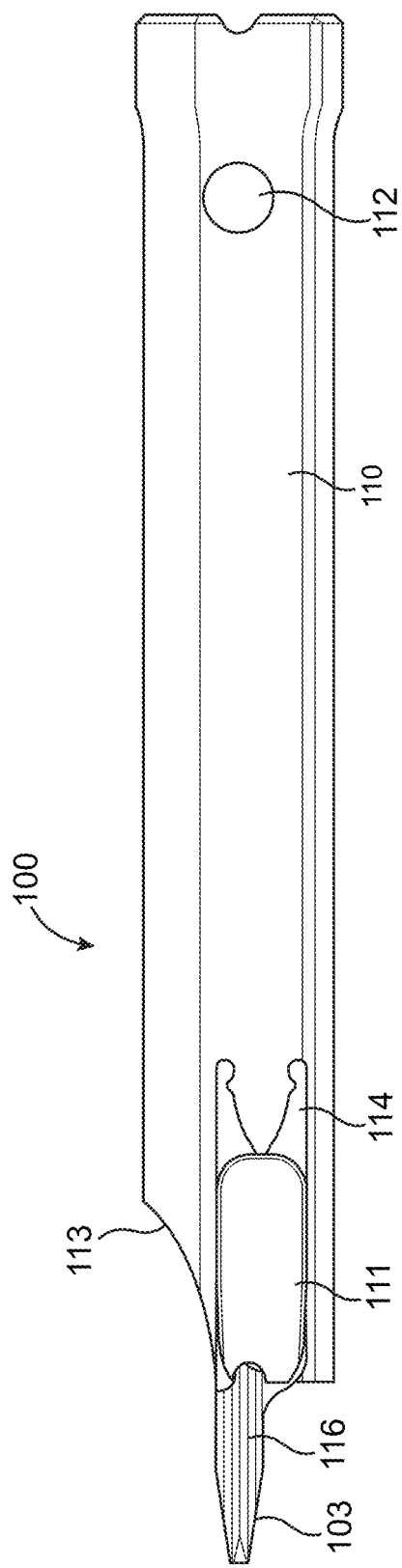
FIG. 2B is a side view of the radiolucent tube of FIG. 2A.
Figure 2C:
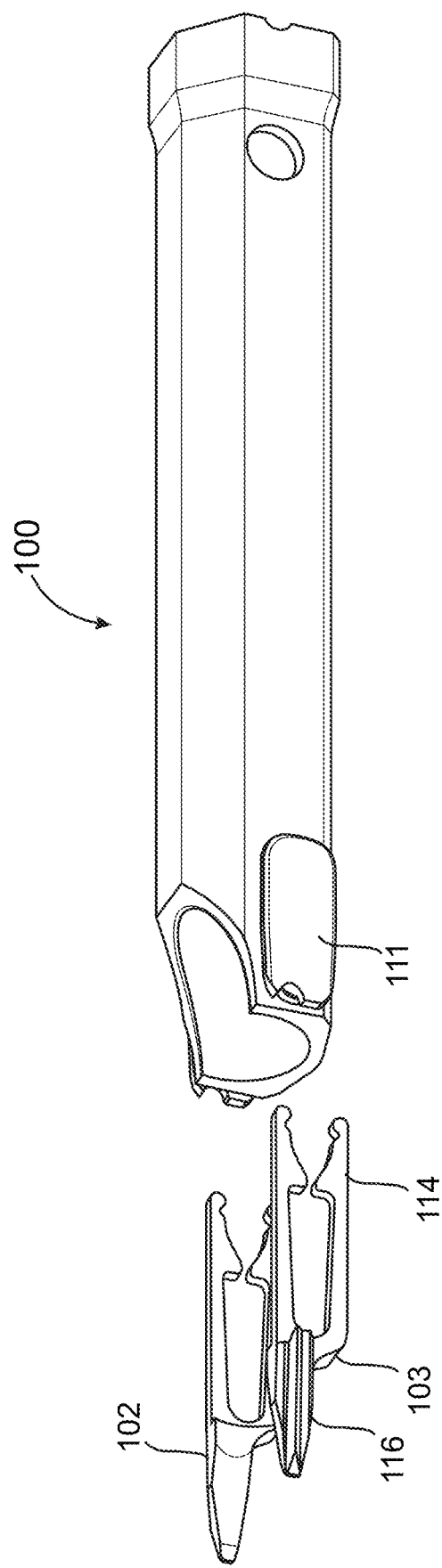
FIG. 2C is an exploded perspective view of the radiolucent tube of FIG. 2A.

FIGS. 2A-2C provide another embodiment of a radiolucent tube 100. Tube 100 is a radiolucent surgical operating tool for minimally invasive sacroiliac fusion surgery and includes a hollow body 110 made of any material that is radiolucent on x-ray (or other radiographic) images and does not block the visibility of surgical instruments or other objects that enter lumen 117 of tube 100 to do tissue and bone preparation and dissection work followed by implantation of a final implant, such as bone graft material or pins.

Tube 100 has a proximal end with opening 118 that leads into lumen 117 of tube 100, and a distal end with opening 119 that leads out of lumen 117 of tube 100. Various objects can be passed through lumen 117 of tube 100, and because tube 100 is made of a radiolucent material, those objects are visible and can be visualized with x-ray imaging. Thus, they are visible in radiographic images of tube 100. At the distal end of tube 100 are removable anchoring tips (or blades) 102 and 103. Removable anchoring tips 102 and 103 have an outer side or surface and an inner side or surface. The outer side or surface of anchoring tips 102 and 103 have channels 116 formed therein. Channels 116 are configured to secure anchoring tips 102 and 103 to the sacroiliac joint by cutting into the bone or cartilage at the joint when distal end 119 of tube 100 is forced into the joint. Tube 100 has a main hollow body 110, which is radiolucent. Tube 100 has mountings 111, one mounting 111 on each side of main hollow body 110. Removable anchoring tips 102 and 103 are mounted to main body 110 by being clipped onto mountings 111 with clips 114. Clips 114 and mountings 111 form a quick-change retaining mechanism. Two opposing arms of each of clips 114 can bend slightly away from each other when forced apart from each other using a tool. By forcing the two opposing arms of clips 114 away from each other, anchoring tips 102 and 103 can be detached from mountings 111. Anchoring tips 102 and 103 can be attached to mountings 111 by sliding the opposing arms of clips 114 over mountings 111, which securely attaches anchoring tips 102 and 103 to mountings 111 unless a force is applied to spread the two opposing arms of clips 114 away from each other while applying a pushing force in the distal direction to push clips 114 off of mountings 111. This forms a quick change retaining/removing mechanism for anchoring tips 102 and 103. Main body 110 has attachment slots 112 (one on each side of hollow main body 110) to which surgical tools or rods can be attached in order to insert or remove tube 100 from a surgical site. Slots 112 also serve as visual references that allow laser marked reference points to be visible of other surgical tools entering lumen 117 of tube 100. While tube 110 is radiolucent, anchoring tips 102 and 103 may also be radiolucent. Alternatively, anchoring tips 102 and 103 can be made of a material that is radiopaque, such as various medical/surgical grade metals, which allows them to be visible in x-ray or other radiographic images.

The present invention also includes a method of performing a surgical procedure using a radiolucent tube to guide surgical instruments, surgical guides and pins, and various implants. The method includes locating a site of intervention using x-ray or other form of radiographic imaging; inserting a guide pin through an incision and advancing a distal end of the guide pin to the site of intervention; guiding an open distal end of a radiolucent tube (e.g., tube 1 or tube 100) over the guide pin and advancing the tube to the site of intervention, wherein the guide pin is visible in a radiographic image of the tube and guide pin even though the guide pin is inside a lumen (e.g., 17 or 117) of the tube; securing the distal end of the radiolucent tube to the site of intervention; and inserting one or more objects through an open proximal end of the radiolucent tube and advancing said one or more objects through the lumen of the tube to the site of intervention, wherein said one or more objects are visible in a radiographic image of the tube even when said one or more objects are inside the lumen of the tube.

In yet another embodiment, a method of performing a sacroiliac fusion procedure is provided. The method includes locating the sacroiliac joint using radiographic imaging; inserting a guide pin through an incision on the subject and advancing the guide pin to the sacroiliac joint; and providing a tube (e.g., tube 1 or tube 100) that allows x-ray visualization of objects passing through the tube. The tube has a proximal end with an opening; a distal end with an opening; one or more mounts on the distal end of the tube for attaching removable anchoring tips thereto; and one or more removable anchoring tips attached to the distal end of the tube with the one or more mounts. The tube is made of a material that is radiolucent and permits x-ray visualization of objects that are passed through the tube. The method further includes guiding the distal opening (e.g., distal opening 19 of tube 1 or distal opening 119 of tube 100) of the radiolucent tube over the guide pin and advancing the tube to the site of sacroiliac joint, wherein the guide pin is visible in the radiographic image of the tube and guide pin even though the guide pin is inside a lumen of the tube; securing the distal end of the radiolucent tube to the sacroiliac joint by forcing the anchoring tips (e.g., anchoring tips 2 and 3 of tube 1 or anchoring tips 102 and 103 of tube 100) into the sacroiliac joint; and inserting one or more objects through the proximal opening off the radiolucent tube and advancing said one or more objects through the lumen of the tube to the sacroiliac joint, wherein said one or more objects are visible in a radiographic image of the tube even when said one or more objects are inside the lumen of the tube. The objects can be various surgical instruments, guide pins, or implants. In one embodiment, a surgical plunger is used to push a bone graft through lumen 17 of tube 1 or lumen 117 of tube 100, with both the plunger and the bone graft being visible in radiographic images taken during the surgical procedure. The bone graft is pushed into the sacroiliac joint.

In another embodiment, a method of performing a poster sacroiliac joint fusion procedure is provided. The method includes locating the sacroiliac joint under x-ray imaging; making a small incision in the patient and inserting a guide pin and advancing the guide pin to the sacroiliac joint while x-ray imaging; passing a joint-finder over the guide pin and advancing the joint finder through the incision and to the sacroiliac joint over the guide pin while x-ray imaging; using a strike cap and mallet to force the joint finder into the sacroiliac joint (the strike cap is placed against the proximal end of the joint finder and the mallet is used to strike the strike cap, which then pushes the joint finder into the sacroiliac joint); guiding distal end 119 of hollow tube 110 over the joint finder and advancing tube 100 through the incision as the joint finder move into lumen 117 of hollow tube 110; using the strike cap and mallet to force anchoring tips 102 and 103 into the sacroiliac joint (the strike cap is placed against the proximal end of radiolucent tube 100 and the mallet is used to strike the strike cap, which then pushes radiolucent tube 100 toward sacroiliac joint with anchoring tips 102 and 103 being forced into the sacroiliac joint); securing tube 100 to the sacroiliac joint using channels 116 of anchoring tips 102 and 103 that cut into bone; removing the joint finder and guide pin thus leaving a radiolucent working channel formed by the radiolucent tube 100 allowing for total visualization of the anatomy of the patient and the sacroiliac joint as well as sacroiliac joint landmarks; inserting a decorticator into lumen 117 of tube 110 through the proximal end opening 118 of tube 110, and decorticating bone at the sacroiliac joint; removing the decorticator; using a funnel and plunger inserted into the lumen 117 of tube 110 through the proximal end opening 118 of tube 110 to introduce biologics into the sacroiliac joint; introducing a bone graft, such as the Silo™ bone graft made by Aurora Spine® through lumen 117, which again forms a radiolucent working channel, and pushing the bone graft into the biologic material such that the biologic material is forced into working channels formed into the Silo™ bone graft, thus securing the bone graft in place within the sacroiliac joint; and optionally introducing additional biologics after the bone graft has been placed in the sacroiliac joint. All of these steps are performed under x-ray imaging and all of the instruments, bone graft and biologic material are visible in x-ray images, because tube 110 is radiolucent and objects within it are visible in x-ray images of tube 110. The bone graft material can be any type of bone graft material suitable for the sacroiliac joint.

In another embodiment, a kit for performing a sacroiliac fusion procedure is provided. The kit can include a guide pin, a joint finder, a radiolucent surgical operating tool, such as radiolucent tube 100, biologics for bone fusion, bone graft material, such as the Silo™ bone graft by Aurora Spine®, and instructions for use during a sacroiliac fusion procedure including one or more of the following steps:

i. locating the sacroiliac joint under x-ray imaging;
    ii. making a small incision in the patient and inserting a guide pin and advancing the guide pin to the sacroiliac joint;
    iii. passing a joint-finder over the guide pin and advancing the joint finder through the incision and to the sacroiliac joint over the guide pin;
    iv. using a strike cap and mallet to force the joint finder into the sacroiliac joint (the strike cap is placed against the proximal end of the joint finder and the mallet is used to strike the strike cap, which then pushes the joint finder into the sacroiliac joint);
    v. guiding distal end 119 of hollow tube 110 over the joint finder and advancing tube 100 through the incision as the joint finder moves into lumen 117 of hollow tube 110;
    vi. using the strike cap and mallet to force anchoring tips 102 and 103 into the sacroiliac joint (the strike cap is placed against the proximal end of radiolucent tube 100 and the mallet is used to strike the strike cap, which then pushes radiolucent tube 100 toward sacroiliac joint with anchoring tips 102 and 103 being forced into the sacroiliac joint);
    vii. securing tube 100 to the sacroiliac joint using channels 116 of anchoring tips 102 and 103 that cut into bone;
    viii. removing the joint finder and guide pin thus leaving a radiolucent working channel formed by the radiolucent tube 100 allowing for total visualization of the anatomy of the patient and the sacroiliac joint as well as sacroiliac joint landmarks;

ix. inserting a decorticator into lumen 117 of tube 110 through the proximal end opening 118 of tube 110, and decorticating bone at the sacroiliac joint;

x. removing the decorticator;

xi. using a funnel and plunger inserted into the lumen 117 of tube 110 through the proximal end opening 118 of tube 110 to introduce biologics into the sacroiliac joint;

xii. introducing a bone graft, such as the Silo™ bone graft made by Aurora Spine® through lumen 117, which again forms a radiolucent working channel, and pushing the bone graft into the biologic material such that the biologic material is forced into working channels formed into the Silo™ bone graft, thus securing the bone graft in place within the sacroiliac joint; and xiii. optionally introducing additional biologics after the bone graft has been placed in the sacroiliac joint.

xiv. The steps set forth above are performed under x-ray imaging of the radiolucent tube 100 and the sacroiliac joint, with the radiolucent tube allowing radiographic visibility of all of the instruments and implants that are passed through tube 100.

In another embodiment, a kit for performing a sacroiliac fusion procedure is provided. The kit can include a guide pin, a joint finder, a radiolucent surgical operating tool, such as radiolucent tube 100, biologics for bone fusion, bone graft material, such as the Silo™ bone graft by Aurora Spine®, and instructions for use during a sacroiliac fusion procedure including one or more of the following steps:

i. locating the sacroiliac joint using radiographic imaging;

ii. inserting a guide pin through an incision on the subject and advancing the guide pin to the sacroiliac joint; and iii. providing a tube that allows x-ray visualization of objects passing through the tube. The tube has a proximal end with an opening; a distal end with an opening; one or more mounts on the distal end of the tube for attaching removable anchoring tips thereto; and one or more removable anchoring tips attached to the distal end of the tube with the one or more mounts. The tube is made of a material that is radiolucent and permits x-ray visualization of objects that are passed through the tube.

iv. guiding the distal opening of the radiolucent tube over the guide pin and advancing the tube to the site of sacroiliac joint, wherein the guide pin is visible in the radiographic image of the tube and guide pin even though the guide pin is inside a lumen of the tube;

v. securing the distal end of the radiolucent tube to the sacroiliac joint by forcing the anchoring tips into the sacroiliac joint; and vi. inserting one or more objects through the proximal opening off the radiolucent tube and advancing said one or more objects through the lumen of the tube to the sacroiliac joint, wherein said one or more objects are visible in a radiographic image of the tube even when said one or more objects are inside the lumen of the tube.

While the is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

We claim:

1. An apparatus for sacroiliac fusion surgery comprising:
   a tube that allows x-ray visualization of objects passing through the tube, said tube having a proximal end with an opening and a distal end with an opening;
   one or more anchoring tips at the distal end of the tube, wherein the one or more anchoring tips each have an outer side and an inner side, and the outer sides have channels formed thereon, wherein the channels are configured to secure the anchoring tips in a sacroiliac joint;
   wherein the tube is made of a material that is radiolucent and permits x-ray visualization of objects that are passed through the tube.

2. The apparatus of claim 1, wherein the anchoring tips are radiopaque and are visible in radiographic images of the apparatus.

3. A method of performing a sacroiliac fusion procedure on a subject comprising:
   locating the sacroiliac joint using radiographic imaging;
   inserting a guide pin through an incision on the subject and advancing the guide pin to the sacroiliac joint;
   providing a tube that allows x-ray visualization of objects passing through the tube, said tube comprising:
      a proximal end with an opening;
      a distal end with an opening;
      one or more anchoring tips at the distal end of the tube;
      wherein the tube is made of a material that is radiolucent and permits x-ray visualization of objects that are passed through the tube;
   guiding the distal opening of the radiolucent tube over the guide pin and advancing the tube to the site of sacroiliac joint, wherein the guide pin is visible in the radiographic image of the tube and guide pin even though the guide pin is inside a lumen of the tube; and
   securing the distal end of the radiolucent tube to the sacroiliac joint by forcing the anchoring tips into the sacroiliac joint.

4. The method of claim 3, further comprising the step of inserting one or more objects through the proximal opening of the radiolucent tube and advancing said one or more objects through the lumen of the tube to the sacroiliac joint, wherein said one or more objects are visible in a radiographic image of the tube even when said one or more objects are inside the lumen of the tube.

5. The method of claim 4, wherein the one or more objects is bone graft material.

6. The method of claim 4, wherein the one or more objects is a plunger or other orthopedic tool.

7. The method of claim 3, wherein the one or more anchoring tips each have an outer side and an inner side, and the outer sides have channels formed thereon, wherein the channels are configured to secure the anchoring tips in the sacroiliac joint.

8. The method of claim 3, wherein the anchoring tips are radiopaque and are visible in a radiographic image of the radiolucent tube.

* * * * *